US010253058B2

United States Patent
Pottie et al.

(10) Patent No.: US 10,253,058 B2
(45) Date of Patent: Apr. 9, 2019

(54) ALKYLGLYCOSIDE SULFOMETHYLSUCCINATE SURFACTANTS

(71) Applicant: BASF SE, Ludwigshafen (DE)

(72) Inventors: Laurence Pottie, Cologne (DE); Eva Max, Bayreuth (DE); Frank Clasen, Hilden (DE); Christian Schade, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 133 days.

(21) Appl. No.: 15/318,049

(22) PCT Filed: Jun. 12, 2015

(86) PCT No.: PCT/EP2015/063128
§ 371 (c)(1),
(2) Date: Dec. 12, 2016

(87) PCT Pub. No.: WO2015/197377
PCT Pub. Date: Dec. 30, 2015

(65) Prior Publication Data
US 2017/0137452 A1 May 18, 2017

(30) Foreign Application Priority Data

Jun. 23, 2014 (EP) .................................... 14173378

(51) Int. Cl.
*C11D 1/12* (2006.01)
*C11D 3/22* (2006.01)
(Continued)

(52) U.S. Cl.
CPC ............. *C07H 15/04* (2013.01); *A61K 8/046* (2013.01); *A61K 8/442* (2013.01); *A61K 8/60* (2013.01);
(Continued)

(58) Field of Classification Search
CPC .. C11D 1/12; C11D 1/662; C11D 3/22; C11D 3/226; C11D 3/228; A61K 8/602; A61K 8/604; C07H 15/04
See application file for complete search history.

(56) References Cited

U.S. PATENT DOCUMENTS 5,908,928 A 6/1999 Milstein et al.
7,087,571 B1 8/2006 O'Lenick, Jr. et al.
(Continued)

FOREIGN PATENT DOCUMENTS

CA 1338237 C 4/1996
FR 2785794 A1 5/2000
(Continued)

OTHER PUBLICATIONS

Ding, J., et al., "Synthesis and Characterization of Sodium Nonylphenol Ethoxylate(10) Sulfoitaconate Esters." *Journal of Surfactants and Detergents* (2011), vol. 14, No. 1, pp. 43-49.
(Continued)

*Primary Examiner* — Brian P Mruk
(74) *Attorney, Agent, or Firm* — Marshall, Gerstein & Borun LLP

(57) ABSTRACT

The present invention relates to an alkyl glycoside sulfomethylsuccinate having the formula $R^1$-O-$S_n$-$R^2$ wherein $R^1$ is an alkyl radical having 6 to 30 carbon atoms, S is a monosaccharide moiety, and $R^2$ is a sulfomethylsuccinate moiety. Furthermore the present invention relates to a process for making this alkyl glycoside sulfomethylsuccinate and to an alkyl glycoside itaconate which is a useful intermediate for use in this process. Furthermore the present invention relates to a cosmetic composition comprising the alkyl glycoside sulfomethylsuccinate and to the use of the alkyl glycoside sulfomethylsuccinate for improving the foam stability of a cosmetic composition.

17 Claims, 1 Drawing Sheet

(51) Int. Cl.
*A61K 8/60* (2006.01)
*C07H 15/04* (2006.01)
*A61K 8/04* (2006.01)
*A61K 8/44* (2006.01)
*A61Q 5/02* (2006.01)
*A61Q 19/10* (2006.01)

(52) U.S. Cl.
CPC .............. *A61K 8/602* (2013.01); *A61K 8/604* (2013.01); *A61Q 5/02* (2013.01); *A61Q 19/10* (2013.01); *A61K 2800/48* (2013.01); *A61K 2800/52* (2013.01)

(56) References Cited

U.S. PATENT DOCUMENTS

2011/0312865 A1* 12/2011 Hodge .................... C11D 1/123
510/218
2015/0368284 A1* 12/2015 Pottie ..................... C07H 15/04
510/127

FOREIGN PATENT DOCUMENTS

| JP | S58132092 A | 8/1983 |
| WO | WO-90/03977 A1 | 4/1990 |
| WO | WO-97/42299 A1 | 11/1997 |
| WO | WO-2011/109047 A2 | 9/2011 |

OTHER PUBLICATIONS

International Search Report for PCT Patent Application No. PCT/EP2015/063128, dated Aug. 8, 2015.

* cited by examiner

|   | 2 | 30 | 60 |
|---|---|----|----|
| A |  | 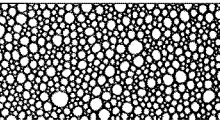 | 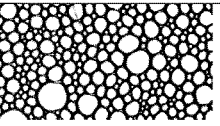 |
| B |  | 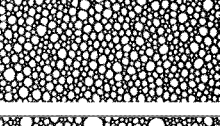 | 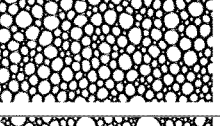 |
| C | 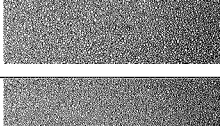 | 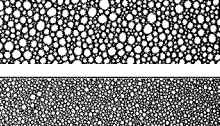 | 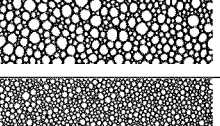 |
| D | 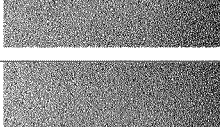 | 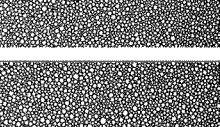 | 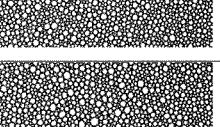 |
| E |  | 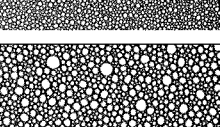 | 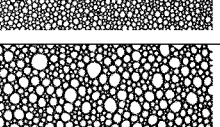 |
| F | 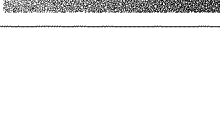 | 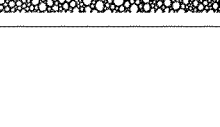 | 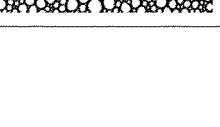 |

ALKYLGLYCOSIDE SULFOMETHYLSUCCINATE SURFACTANTS

CROSS-REFERENCE TO RELATED APPLICATIONS

This is the U.S. national phase of International Patent Application No. PCT/EP2015/063128, filed Jun. 12, 2015, which claims the benefit of European Patent Application No. 14173378.2, filed Jun. 23, 2014.

The present invention relates to an alkyl glycoside sulfomethylsuccinate having the formula $R^1$-O-$S_n$-$R^2$ wherein $R^1$ is an alkyl radical having 6 to 30 carbon atoms, S is a monosaccharide moiety, and $R^2$ is a sulfomethylsuccinate moiety. Furthermore the present invention relates to a process for making this alkyl glycoside sulfomethylsuccinate and to an alkyl glycoside itaconate which is a useful intermediate for use in this process. Furthermore the present invention relates to a cosmetic composition comprising the alkyl glycoside sulfomethylsuccinate and to the use of the alkyl glycoside sulfomethylsuccinate for improving the foam stability of a cosmetic composition.

Alkyl glycosides are well known, mild, natural based, non-ionic surfactants. However, they have low foam ability. Many patent applications relate to alkyl glycosides. WO 90/03977 discloses a process for making alkyl glycosides.

Some work has already been done to further modify alkyl glycosides into better foaming anionic surfactants. Examples of such anionic alkyl glycoside derivatives include alkyl glycoside ethercarboxylates, commercially available from BASF SE, Ludwigshafen, Germany, under the trademark Plantapon® LGC. U.S. Pat. No. 5,908,928 discloses alkyl glycoside ethercarboxylates. Alkyl glycosides ethercarboxylates produce increased foam quantity but they involve chloro-acetic acid for their production, which is difficult to handle.

Another type of anionic alkyl glycoside derivative is alkyl glycoside sulfosuccinate. This surfactant type is usually obtained in a two-step modification of alkyl glycosides. Firstly, the alkyl glycoside is reacted with maleic acid anhydride. Upon reaction the anhydride opens generating a carboxylic group. Then a second anionic group is generated by sulfonation of the alkyl glycoside maleate, using for instance sodium sulfite. This process is disclosed in U.S. Pat. No. 7,087,571.

Alkyl glycoside sulfosuccinates are also commercially available, e. g. under the trademark Eucarol® AGE SS from the company Lamberti. Because of its anionic character this surfactant shows improved foaming ability compared to the non-anionic alkyl glycosides.

The alkyl glycoside sulfosuccinates and other anionic alkyl glycoside derivatives are commonly used in cosmetic formulations. This is for example disclosed in FR 2 785 794. The market demand for cosmetic ingredients based on renewable feedstock is constantly increasing. In this context alternatives to alkyl glycoside sulfosuccinates are desired because alkyl glycoside sulfosuccinates are not available based on renewable feedstock as their synthesis requires the use of petro-based maleic acid anhydride.

WO 2011/109047 and J. Ding, B. Song, C. Wang, J. Xu, Y. Wu, J. Surfact Deterg (2011) 14, 43-49, Synthesis and Characterization of sodium Nonylphenol ethoxylate(10) sulfoitaconate esters; and JP 58132092 A disclose alkyl sulofmethylsuccinate surfactants based on fatty alcohols or fatty alcohol ethoxylates. These surfactants comprise a sulfonate group and they are made using itaconic acid anhydride. Itaconic acid anhydride can be obtained by dehydration of itaconic acid, a product obtained by fermentation of various natural feedstocks. The resulting surfactants are called sulfoitaconates or sulfomethylsuccinates, since they only differ by one methyl group from the sulfo-succinate.

The problem underlying the present invention is to provide a surfactant which has good foaming properties and which can be made based on renewable feedstock.

This problem is solved by providing the surfactant according to the present invention. The surfactant according to the present invention is an alkyl glycoside sulfomethylsuccinate having the following formula (I),

wherein $R^1$ is a linear or branched, saturated or unsaturated, primary, secondary or tertiary alkyl radical having 6 to 30 carbon atoms, S is a monosaccharide moiety, n is 1 to 5, and $R^2$ is a sulfomethylsuccinate moiety according to formula (IIa) or according to formula (IIb),

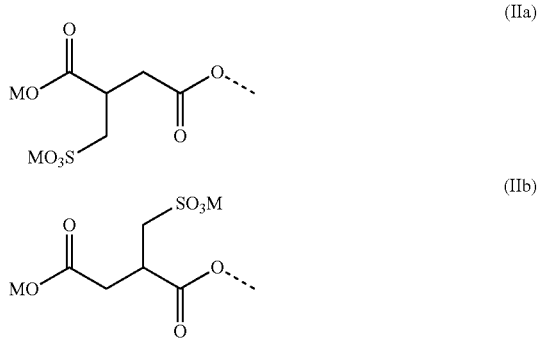

wherein M is H or any cation.

If M bears a charge z+ which is higher than 1+ then there is only 1/z part of this ion present to neutralize the negative charge of the —COO⁻ group and of the —$SO_3^-$ group respectively.

This alkyl glycoside sulfomethylsuccinate is a subject of the present invention.

According to the present invention the term alkyl glycoside means the reaction product of monosaccharides and fatty alcohols. A fatty alcohol is a linear, primary monoalkanol having 6 to 22 carbon atoms, optionally comprising up to 3 double bonds. A monosaccharide can be an aldose or a ketose, for example glucose, fructose, mannose, galactose, talose, gulose, allose, altrose, idose, arabinose, xylose, lyxose or ribose. The aldoses are preferably used by virtue of their better reactivity. Among the aldoses, glucose is particularly suitable because it is readily obtainable and available in industrial quantities. The alkyl glycosides produced with glucose are alkyl glucosides. Alkyl glycosides, depending on the specific process for making them, can comprise oligosaccharide moieties. Therefore, the terms alkyl oligoglycoside, alkyl polyglycoside, alkyl oligosaccharide and alkyl polysaccharide are used for alkyl glucosides in which an alkyl radical is attached to more than one glycose residue, i.e. to a poly- or oligosaccharide residue. These names are regarded as synonymous with one another. Accordingly, an alkyl monoglycoside comprises a monosaccharide moiety. Since mixtures are generally obtained in the acid-catalyzed reaction of sugars and fatty alcohols, the name alkyl glycoside is used in the following both for alkyl mono-glycosides and also for alkyl poly- or oligo-glycosides and, in particular, mixtures thereof. Alkyl glycosides have the formula $R^1$-O-$S_n$-H, wherein $R^1$ is an alkyl moiety derived from a fatty alcohol which is bound to the mono- or oligo-saccharide moiety. It is assumed that this bond is an acetal bond, it is also conceivable that it is a hemiacetal bond or an ether bond. The degree of oligomerization of the saccharide moiety is denoted by n. Values between 1 and 5 (on average) are common. The average is a number average. The H in the formula is an H of an OH-group of the saccharide moiety. In the alkyl glycoside sulfomethylsuccinate according to the present invention this H is replaced by a sulfomethylsuccinate moiety which is bound by one of its two COOH-groups to the saccharide moiety. It is assumed that this bond is an ester bond (i. e. the OH-group is an alcoholic OH-group), although it is also conceivable that the COOH-group of the sulfomethylsuccinate moiety is bound to an OH-group of the saccharide moiety which is derived from its aldehyde or its ketone functionality.

In any case, there is no peroxo-group in the alkyl glycoside sulfomethylsuccinate having formula (I): $R^1$-O-$S_n$-$R^2$. The alkyl glycosides having the formula $R^1$-O-$S_n$-H, wherein the H in this formula is an H of an OH-group of the saccharide moiety, react with itaconic acid under elimination of water so that the OH-group together with a COOH-group react to a COO-group. This means that the O-atom of the COO-group in formula (IIa) and (IIb) is bound to a C-atom of the $S_n$-moiety.

Instead of an alkyl glycoside derived from a fatty alcohol an alkyl glycoside derived from another mono-alcohol having a sufficiently long and therefore lipophilic alkyl chain can be used to make an alkyl glycoside sulfomethylsuccinate according to the present invention.

According to the present invention $R^1$ is a linear or branched, saturated or unsaturated, primary, secondary or tertiary alkyl radical having 6 to 30 carbon atoms. In one embodiment of the present invention $R^1$ is a linear, primary alkyl radical having 6 to 22 carbon atoms, optionally comprising up to 3 double bonds, i. e. $R^1$ is derived from a fatty acohol. In a more specific embodiment of the present invention $R^1$ is a linear, primary alkyl radical having 8 to 18 carbon atoms, optionally comprising up to 3 double bonds. More specifically $R^1$ is a linear, primary alkyl radical having 6 to 20 carbon atoms, optionally comprising up to 3 double bonds. More specifically $R^1$ is a linear, primary alkyl radical having 8 to 14 carbon atoms, optionally comprising up to 3 double bonds. More specifically $R^1$ is a saturated, linear, primary alkyl radical having 8 to 14 carbon atoms.

According to the present invention S is a monosaccharide moiety. In one embodiment of the present invention S is an aldose moiety. In a more specific embodiment of the present invention S is an aldose moiety having 6 carbon atoms. In a more specific embodiment of the present invention S is glucose moiety.

According to the present invention n is 1 to 5. In one embodiment of the present invention n is 1 to 1.5.

According to the present invention $R^2$ is a sulfomethylsuccinate moiety according to formula (IIa) or according to formula (IIb),

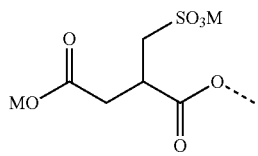
(IIa)

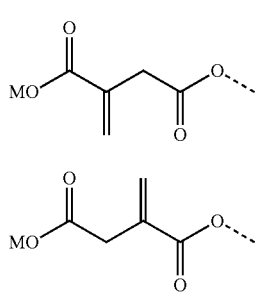
(IIb)

wherein M is H or any cation. In one embodiment of the present invention M is selected from the group consisting of H, an alkali metal cation, $NH_4^+$ and mixtures thereof. In a more specific embodiment of the present invention M is selected from the group consisting of H, $Na^+$, $K^+$, $NH_4^+$ and mixtures thereof.

One embodiment of the present invention is the alkyl glycoside sulfomethylsuccinate according to the present invention, wherein $R^1$ is a saturated, linear, primary alkyl radical having 8 to 14 carbon atoms, S is glucose moiety, n is 1 to 1.5, and M is selected from the group consisting of H, $Na^+$, $K^+$, $NH_4^+$ and mixtures thereof.

Another subject of the present invention is a process for making the alkyl glycoside sulfomethylsuccinate according to the present invention comprising a) reacting an alkyl glycoside $R^1$-O-$S_n$-H, wherein $R^1$, S and n have the meaning defined in any of claims 1 to 10, with itaconic acid, optionally in the presence of a catalyst, or with itaconic acid anhydride, optionally in the presence of a catalyst, so that an alkyl glycoside itaconate is obtained, and b) reacting the alkyl glycoside itaconate with a sulfonating agent, preferably with a sulfite salt or with sulfurous acid, more preferably with sodium sulfite, so that the alkyl glycoside sulfomethylsuccinate according to any of claims 1 to 10 is obtained.

The catalyst that may be used in step a described in the previous paragraph can be a catalyst that is appropriate for an esterification. Catalysts that can be used include, for example, acidic catalysts like alkyl sulfonic acid and in particular methane sulfonic acid, sulfuric acid or phosphoric acid, or metal ion based catalyst like zinc oxide, zinc acetate or zinc oxalate.

Another subject of the present invention is an alkyl glycoside itaconate which can be used as intermediate in the process for making the alkyl glycoside sulfomethylsuccinate according to the present invention. This alkyl glycoside itaconate is an alkyl glycoside itaconate having the following formula (I), $$R^1\text{-O-}S_n\text{-}R^3 \qquad (I)$$

wherein $R^1$, S and n have the meaning defined in any of claims 1 to 10, and $R^3$ is an itaconate moiety according to formula (IIIa) or according to formula (IIIb), (IIIa)

(IIIb)

Another subject of the present invention is a cosmetic composition, preferably a shampoo or a shower gel, comprising the alkyl glycoside sulfomethylsuccinate according to the present invention (preferably in an amount of from 0.01 to 30% by weight, more preferably 0.5 to 20% by weight). In a more specific embodiment of the present invention this cosmetic composition is a shampoo or a shower gel, wherein this shampoo or shower gel comprises an anionic surfactant different from the alkyl glycoside sulfomethylsuccinate (preferably in an amount of from 0.01 to 30% by weight), and wherein this shampoo or shower gel preferably comprises a nonionic surfactant (preferably in an amount of 0.01 to 30% by weight).

Another subject of the present invention is the use of the alkyl glycoside sulfomethylsuccinate according to the present invention for improving the foam stability of a cosmetic composition, preferably of a shampoo or a shower gel, more preferably of a shampoo or a shower gel as defined in the preceding paragraphs.

The alkyl glycoside sulfomethylsuccinate according to the present invention can be used in any kind of formulation. Since it is mild to the skin it is particularly interesting for cosmetic or home care formulations. It can be used in mild foaming formulations such as shampoos or shower gels. In particular it can be used as primary or co-surfactants in formulations based, mostly or exclusively, on products based on renewable feedstock.

The surfactant according to the present invention has good foaming properties. In particular, it was found that it generates foam of superior quality, i.e. foam with smaller bubbles and finer bubble size distribution than other anionic derivatives of alkyl glycosides, e. g. alkyl glycoside sulfosuccinates. Foam having these properties provides a nicer feeling for the user. This could be measured on test-panels. Besides, it was also found that foam of solutions of the surfactant according to the present invention has a better stability, which means that it takes longer times before the foam structure coarsens and the bubble size increases compared to other surfactants that have been tested. This property can be advantageous in applications were long lasting foam is required.

Another advantage of the present invention is that itaconic acid is based on renewable feedstock.

Another advantage of the present invention is that that a higher viscosity can be achieved in some mild formulations which are usually difficult to thicken (viscosity values compared to the same formulations containing alkyl glycoside sulfosuccinate). Itaconic acid itself is known to have antimicrobial activity. Therefore it seems not unlikely that the surfactant of the present invention or formulations containing the surfactant of the present invention may have antimicrobial activity, too.

EXAMPLES

In the following % means % by weight unless specified differently.

Examples

Synthesis

Example 1

Preparation of an Alkyl Glucoside Sulfomethylsuccinate Using Itaconic Acid 495.0 g $C_{12/14}$-alkyl glucoside (Plantacare® 1200 UP: 50.8% active matter, 600 mmol) were poured in a 2 L three-neck-flask, equipped with a stirrer, a distillation condenser and a nitrogen connection. After adjusting the pH to a value of 7.6 using 8.2 g of HCl (37% solution), 50.4 g of a $C_{12/14}$-fatty alcohol (Lorol® $C_{12}$-$C_{14}$ Spezial, 260 mmol) were added. The mixture was then stirred under $N_2$ flow and heated to 120° C. using an oil bath. The water contained in the mixture was distilled, at first under room atmosphere, then carefully applying vacuum (up to 20 mbar). After complete water removal 134.2 g itaconic acid (1032 mmol, Aldrich, purity>99%) were added and the reaction was continued under vacuum. The acid value was controlled each hour until a value between 110 and 130 $mg_{KOH}$/g was reached. The mixture was then cooled to 85° C. and a 100.0 g sample was extracted. 467.4 g of a $Na_2SO_3$ aqueous solution (86.7 g, 688 mmol $Na_2SO_3$) was then added to the rest of the mixture, which was then stirred for further 4 h. Finally, the excess sulfite was oxidized to sulfate using a 35% aqueous $H_2O_2$ solution.

TABLE 1

Analysis of the alkyl glycoside sulfomethylsuccinate

| | Content [%] | Method |
| --- | --- | --- |
| $SO_3^{2-}$ | <0.05 | High Performance Ion Chromatography (HPIC) |
| $SO_4^{2-}$ | 0.7 | |
| sulfomethylsuccinic acid | 9.1 | High Performance Liquid Chromatography (HPLC) |
| $C_{12/14}$-alkyl glucoside | 8.2 | Gas Chromatography (GC) |
| Alkyl glucoside conversion | 63.5 | % conversion = $100 - \left( \frac{\% \text{ not reacted alkyl glucoside} \times 100}{\% \text{ primarily used alkyl glucoside}} \right)$ |
| Water | 48.5 | Karl Fischer (ISO 4317) |

Example 2

Preparation of an Alkyl Glucoside Sulfomethylsuccinate Using Itaconic Acid Anhydride 247.5 g $C_{12/14}$-alkyl glucoside (Plantacare® 1200 UP: 50.8% active matter, 300 mmol) were poured in a 1 L three-neck-flask, equipped with a stirrer, a distillation condenser and a nitrogen connection. After adjusting the pH to a value of 6.7 using 4.1 g of HCl (37% aqueous solution), 50.4 g of a $C_{12/14}$-fatty alcohol (Lorol® $C_{12}$-$C_{14}$ Spezial, 260 mmol) were added. The mixture was then stirred under $N_2$ flow and heated to 120° C. using an oil bath. The water contained in the mixture was distilled, at first under room atmosphere, then carefully applying vacuum (up to 20 mbar). After complete water removal 57.8 g of itaconic acid anhydride (516 mmol, China Jiangsu Int'l Economic and technical cooperation group, LTD/98.8%) were added and the reaction was continued under vacuum. The acid value was controlled each hour until a value between 110 and 130 $mg_{KOH}$/g was reached. The mixture was then cooled to 85° C. Then 317.0 g of a $Na_2SO_3$ aqueous solution (67.0 g, 531 mmol $Na_2SO_3$) was added and the mixture was stirred for further 4 h. Finally, the excess sulfite was oxidized to sulfate using a 35% aqueous $H_2O_2$ solution.

TABLE 2

Analysis of the alkyl glycoside sulfomethylsuccinate

| | Content [%] | Method |
|---|---|---|
| $SO_3^{2-}$ | <0.05 | High Performance Ion Chromatography (HPIC) |
| $SO_4^{2-}$ | 2.2 | |
| Sulfo-Methylsuccinic acid | 11.3 | High Performance Liquid Chromatography (HPLC) |
| $C_{12/14}$-alkyl glucoside | 11.8 | Gas Chromatography (GC) |
| Alkyl glucoside conversion | 50.7 | % conversion = 100 − $\left(\frac{\% \text{ not reacted alkyl glucoside} \times 100}{\% \text{ primarily used alkyl glucoside}}\right)$ |
| Water | 47.0 | Karl Fischer (ISO 4317) |

Example 3

(Comparative Example) Preparation of Alkyl Glucoside Sulfosuccinate Using Maleic Acid Anhydride (Synthesis Under the Same Condition as in Example 2)

247.5 g $C_{12/14}$-alkyl glucoside (Plantacare® 1200: 50.8% active matter, 300 mmol) were poured in a 1 L three-neck-flask, equipped with a stirrer, a distillation condenser and a nitrogen connection. After adjusting the pH to a value of 6.7 using 4.0 g of HCl (37% solution), 25.2 g of a $C_{12/14}$-fatty alcohol (Lorol® $C_{12}$-$C_{14}$ Spezial, 130 mmol) were added. The mixture was then stirred under $N_2$ flow and heated to 120° C. using an oil bath. The water contained in the mixture was distilled, at first under room atmosphere, then applying vacuum (up to 20 mbar). After complete water removal the mixture was cooled down to approximately 90° C. and 50.8 g maleic acid anhydride (516 mmol, Merck, purity>99%) were added. The reaction was continued at 90° C. for 2 h, after which the mixture was cooled down to 85° C. 182.0 g of a $Na_2SO_3$ aqueous solution (67.0 g, 531 mmol $Na_2SO_3$) were then added and the mixture was stirred for further 4 h. Finally, the excess sulfite was oxidized to sulfate using a 35% aqueous $H_2O_2$ solution.

TABLE 3

Analysis of the alkyl glycoside sulfosuccinate

| | Content [%] | Method |
|---|---|---|
| $SO_3^{2-}$ | 0.14 | High Performance Ion Chromatography (HPIC) |
| $SO_4^{2-}$ | 0.24 | |
| Sulfosuccinic acid | 3.0 | High Performance Liquid Chromatography (HPLC) |
| $C_{12/14}$-alkyl glucoside | 8.2 | Gas Chromatography (GC) |
| Alkyl glucoside conversion | 66.2 | % conversion = 100 − $\left(\frac{\% \text{ not reacted alkyl glucoside} \times 100}{\% \text{ primarily used alkyl glucoside}}\right)$ |
| Water | 42.5 | Karl Fischer (ISO 4317) |

Examples

Analysis of the Foam of the Solutions of the Surfactants Made

A stock solution of 12% active substance surfactant was prepared and diluted to 0.26%. This dilution mimics typical application concentrations used in personal care. The diluted solution was foamed in hard water (15° dH, pH 5.5) for 5 minutes at a stirring rate of 1300 rpm using a SITA Foam Tester R2000. The produced foam was manually transferred to the measuring cell of the Foam Image Analyzer in which the foam structure was analyzed. The Foam Image Analyzer contains a measuring cell Petri dish (diameter of 90 mm and height of 15 mm). A glass prism was placed in contact with the foam and images of the foam were recorded using a video camera, equipped with a magnifying lens. Images were recorded for a 1 hour period and thus foam stability was evaluated by examining the development of the foam structure with time. Both the foam production and the foam stability were performed at ambient room temperature.

FIG. 1 shows the results. It shows the foam analyzer images of the various alkyl glucoside derivative surfactant solutions testes. Image dimensions are 20 mm×10 mm. In FIG. 1 the following abbreviations are used:

A: Plantacare® 1200 UP (alkyl glucoside)
B: Plantapon® LGC Sorb (alkyl glucoside ether carboxylate)
C: Eucarol® AGE-SS (alkyl glucoside sulfosuccinate)
D: alkyl glucoside sulfomethylsuccinate according to synthesis Example 1
E: alkyl glucoside sulofmethylsuccinate according to synthesis Example 2
F: alkyl glucoside sulfosuccinate according to synthesis Example 3
2: 2 minutes
30: 30 minutes
60: 60 minutes

TABLE 5

Median area of bubbles calculated using the pictures of FIG. 1

| | Median Area/mm² | | |
|---|---|---|---|
| | 2 minutes | 30 minutes | 60 minutes |
| Plantacare ® 1200 UP (alkyl glucoside) | 0.02 | 0.15 | 0.34 |
| Plantapon ® LGC Sorb (alkyl glucoside ether carboxylate) | 0.01 | 0.14 | 0.33 |
| Eucarol ® AGE-SS (alkyl glucoside sulfosuccinate) | 0.01 | 0.06 | 0.11 |
| alkyl glucoside sulofmethylsuccinate according to synthesis Example 1 | 0.01 | 0.03 | 0.05 |
| alkyl glucoside sulfomethylsuccinate according to synthesis Example 2 | 0.01 | 0.03 | 0.05 |
| alkyl glucoside sulfomethylsuccinate according to synthesis Example 3 | 0.02 | 0.14 | 0.33 |

Examples

Viscosity of Formulations

Alkyl glucoside containing cosmetic formulations are usually difficult to thicken to a level acceptable for the consumer perception. Therefore we checked with a typical example the comparative viscosities obtained by thickening formulation of alkyl glucoside anionic derivatives with NaCl and a synthetic thickener (Arlypon® TT). The formulations compositions are given in Table 6. The individual components were weighed and mixed together in water (all given percentages are weight-percentages). After the formulations were bubble-free and conditioned to 30° C., their viscosity was determined using the Brookfield viscometer II+D pro (Spindel S64, 60 rpm).

TABLE 6

Viscosity of formulations containing alkyl glucoside sulfosuccinate or alkyl glucoside sulfomethylsuccinate surfactants

| Ingredient | Structure/INCI | Content in Formulation [%] | |
|---|---|---|---|
| | | Formulation A | Formulation B |
| Eucarol ® AGE-SS | alkyl glucoside sulfosuccinate | 8 | 0 |
| alkyl glucoside sulfomethylsuccinate | according to synthesis Example 1 | 0 | 8 |
| Dehyton ® PK 45 | Cocamidopropyl Betaine | 3 | 3 |
| Texapon ® NSO | Sodiun Laureth Sulfate | 1 | 1 |
| NaCl | — | 3 | 3 |
| Arlypon ® TT | Ethoxylated fatty alcohol (thickener) | 2 | 2 |
| Viscosity eta [mPas] | | 720 | 3569 |

Examples

Formulations

Shower Gel:

| | Ingredient | INCI | Content [% active substance] | | |
|---|---|---|---|---|---|
| | | | 1 | 2 | 3 |
| I | Sulfopon 1216G | Sodium Coco Sulfate | 6.0 | 6.0 | 6.0 |
| | Plantapon LCG Sorb | Sodium Lauryl Glucose Carboxylate (and) Lauryl Glucoside | 3.7 | — | — |
| | alkyl glucoside sulfomethylsuccinate according to synthesis Example 1 | | — | 3.7 | — |
| | alkyl glucoside sulfosuccinate according to synthesis Example 3 | | — | — | 3.7 |
| | Lamesoft PO65 | Cocoglucoside (and) Glyceryl Oleate | 3.0 | 3.0 | 3.0 |
| II | Deionized water | Aqua | 85.6 | 85.6 | 85.6 |
| | Sodium benzoate | | 0.5 | 0.5 | 0.5 |
| | Fragance | | 0.3 | 0.3 | 0.3 |
| III | NaCl | Sodium Chloride | 0.1 | 0.1 | 0.1 |
| IV | Citric acid (50% solution) | Citric Acid | 0.8 (to pH 5.0) | 0.8 (to pH 5.0) | 0.8 (to pH 5.0) |

Kid Shampoo:

| Ingredient | INCI | Content [% active substance] | | |
|---|---|---|---|---|
| | | 4 | 5 | 6 |
| Plantapon LCG Sorb | Sodium Lauryl Glucose Carboxylate (and) Lauryl Glucoside | 5.4 | — | — |
| alkyl glucoside sulfomethylsuccinate according to synthesis Example 1 | | — | 5.4 | — |
| alkyl glucoside sulfosuccinate according to synthesis Example 3 | | — | — | 5.4 |
| Dehyton PK45 | Cocamidopropyl Betaine | 5.2 | 5.2 | 5.2 |
| Lamesoft PO65 | Cocoglucoside (and) Glyceryl Oleate | 2.0 | 2.0 | 2.0 |
| Plantasil Micro | Dicapryl Ether (and) Decyl Glucoside(and) Glyceryl Oleate | 7.0 | 7.0 | 7.0 |
| Sage distillate (Fytosan) | *Salvia Officinalis* Leaf | 10.0 | 10.0 | 10.0 |
| Dissolvines GL 38 (Akzo) | Tetrasodium Glutamate diacetate | 0.05 | 0.05 | 0.05 |
| fragance | | 0.2 | 0.2 | 0.2 |
| Geogard 221 (Lonza) | Dehydroacetic acid (and) Benzyl alcohol | 0.8 | 0.8 | 0.8 |
| NaOH | Sodium Chloride | 0.1 | 0.1 | 0.1 |
| Deionized water | Aqua | 69.25 | 69.25 | 69.25 |

The formulations were mixed with tap water (20 g formulation+80 g water) in a 800 mL glass beaker and warmed up to 30° C. The formulations were foamed by mixing 10 seconds at 2000 rpm. The foam height in the beaker is measured after the mixing is stopped and the foam quality is optically assessed from 1=high quality (dense and stable foam with fine pore) to 4=poor foam quality (dry foam with large pore, easily broken).

| Formulation Number | Foam Height [cm] | Foam quality |
|---|---|---|
| 1 | 8.9 | 3 |
| 2 | 9.0 | 3 |
| 3 | 7.6 | 4 |
| 4 | 8.1 | 2 |
| 5 | 8.3 | 2 |
| 6 | 7.9 | 2 |

The invention claimed is:

1. An alkyl glycoside sulfomethylsuccinate having a formula (I), $$R^1\text{-O-}(Sach)_n\text{-}R^2 \qquad (I)$$

wherein
$R^1$ is a linear or branched, saturated or unsaturated, primary, secondary or tertiary alkyl radical having 6 to 30 carbon atoms,
Sach is a monosaccharide moiety,
n is 1 to 5, and
$R^2$ is a sulfomethylsuccinate moiety according to formula (IIa) or according to formula (IIb),

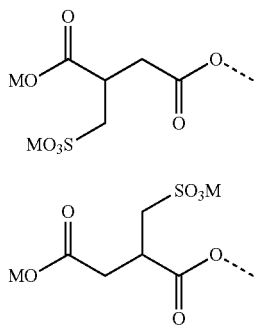

(IIa)

(IIb)

wherein
M is H or any cation.

2. The alkyl glycoside sulfomethylsuccinate according to claim 1, wherein $R^1$ is a linear, primary alkyl radical having 6 to 22 carbon atoms, optionally comprising up to 3 double bonds.

3. The alkyl glycoside sulfomethylsuccinate according to claim 1, wherein $R^1$ is a linear, primary alkyl radical having 8 to 18 carbon atoms, optionally comprising up to 3 double bonds.

4. The alkyl glycoside sulfomethylsuccinate according to claim 1, wherein Sach is an aldose moiety.

5. The alkyl glycoside sulfomethylsuccinate according to claim 4, wherein Sach is an aldose moiety having 6 carbon atoms.

6. The alkyl glycoside sulfomethylsuccinate according to claim 1, wherein Sach is a glucose moiety.

7. The alkyl glycoside sulfomethylsuccinate according to claim 1, wherein n is 1 to 1.5.

8. The alkyl glycoside sulfomethylsuccinate according to claim 1, wherein M is selected from the group consisting of H, an alkali metal cation, $NH_4^+$, and mixtures thereof.

9. The alkyl glycoside sulfomethylsuccinate according to claim 8, wherein M is selected from the group consisting of H, $Na^+$, $K^+$, $NH_4^+$, and mixtures thereof.

10. The alkyl glycoside sulfomethylsuccinate according to claim 1, wherein
   $R^1$ is a saturated, linear, primary alkyl radical having 8 to 14 carbon atoms,
   Sach is a glucose moiety,
   n is 1 to 1.5, and
   M is selected from the group consisting of H, $Na^+$, $K^+$, $NH_4^+$ and mixtures thereof.

11. A process for making the alkyl glycoside sulfomethylsuccinate according to claim 1 comprising
   a) reacting an alkyl glycoside $R^1$-O-$(Sach)_n$-$R^2$, with itaconic acid, optionally in the presence of a catalyst, or with itaconic acid anhydride, optionally in the presence of a catalyst, so that an alkyl glycoside itaconate is obtained, and
   b) reacting the alkyl glycoside itaconate with a sulfonating agent so that the alkyl glycoside sulfomethylsuccinate is obtained.

12. An alkyl glycoside itaconate having a formula (I), $$R^1\text{-O-}S_n\text{-}R^3 \quad (I)$$

wherein $R^1$ is a linear or branched, saturated or unsaturated, primary, secondary or tertiary alkyl radical having 6 to 30 carbon atoms,
S is a monosaccharide moiety,
n is 1 to 5, and
$R^3$ is an itaconate moiety according to formula (IIIa) or according to formula (IIIb),

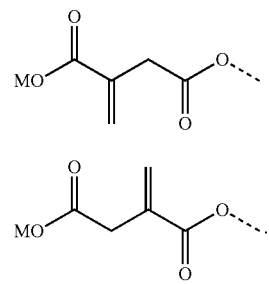

(IIIa)

(IIIb)

13. A cosmetic composition comprising the alkyl glycoside sulfomethylsuccinate according to claim 1, in an amount of from 0.01 to 30% by weight.

14. The cosmetic composition according to claim 13, wherein this cosmetic composition is a shampoo or a shower gel, and wherein this shampoo or shower gel comprises an anionic surfactant different from the alkyl glycoside sulfomethylsuccinate in an amount of from 0.01 to 30% by weight and wherein this shampoo or shower gel optionally comprises a nonionic surfactant.

15. The alkyl glycoside sulfomethylsuccinate according to claim 3, wherein $R^1$ is a linear, primary alkyl radical having 8 to 14 carbon atoms, optionally comprising up to 3 double bonds.

16. The alkyl glycoside sulfomethylsuccinate according to claim 15, wherein $R^1$ is a linear, primary alkyl radical having 8 to 14 carbon atoms.

17. The cosmetic composition according to claim 14, wherein the cosmetic composition further comprises a nonionic surfactant in an amount from 0.01 to 30% by weight.

* * * * *